United States Patent [19]

Sudduth et al.

[11] 3,960,910

[45] June 1, 1976

[54] PROCESS FOR THE PURIFICATION OF GAS STREAMS

[75] Inventors: Jerome R. Sudduth, Pasadena; Donald A. Keyworth, Houston, both of Tex.

[73] Assignee: Tenneco Chemicals, Inc., Saddle Brook, N.J.

[22] Filed: Jan. 6, 1975

[21] Appl. No.: 538,616

[52] U.S. Cl.......................... 260/438.1; 260/429 R; 260/448 R; 260/674 R; 260/677 A
[51] Int. Cl.². ........................................... C07F 1/08
[58] Field of Search............. 260/438.1, 430, 429 R, 260/677 A, 674 R

[56] References Cited
UNITED STATES PATENTS

| | | | |
|---|---|---|---|
| 3,592,865 | 7/1971 | Long et al. | 260/677 A |
| 3,647,843 | 3/1972 | Walker et al. | 260/438.1 |
| 3,651,159 | 3/1972 | Long et al. | 260/438.1 X |
| 3,758,606 | 9/1973 | Horowitz | 260/677 A |
| 3,857,869 | 12/1974 | Turnbo | 260/438.1 |
| 3,868,398 | 2/1975 | Kroll et al. | 260/438.1 |

*Primary Examiner*—Helen M. S. Sneed
*Attorney, Agent, or Firm*—Evelyn Berlow

[57] ABSTRACT

Water, ammonia, and certain other reactive impurities are removed from gas streams that contain such complexible ligands as olefins, acetylenes, aromatics, and carbon monoxide by contacting the gas streams with a purification medium that comprises (a) a bimetallic salt complex having the generic formula,

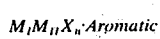

$$M_I M_{II} X_n \cdot Aromatic$$

wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon having 6 to 12 carbon atoms, (b) a monocyclic aromatic hydrocarbon having 6 to 12 carbon atoms, and (c) at least one product of the reaction of the impurities with said bimetallic salt complex.

5 Claims, No Drawings

PROCESS FOR THE PURIFICATION OF GAS STREAMS

This invention relates to a process for the purification of gas streams. More particularly, it relates to a process for the separation of water, ammonia, and certain other reactive impurities from gas streams that contain such complexible ligands as olefins, acetylenes, aromatics, and carbon monoxide.

Bimetallic salt complexes that have the generic formula $M_I M_{II} X_n$·Aromatic, wherein $M_I$ is a Group I-B metal, $M_{II}$ is a Group III-A metal, X is halogen, $n$ is the sum of the valences of $M_I$ and $M_{II}$, and Aromatic is a monocyclic aromatic hydrocarbon having 6 to 12 carbon atoms, are known to be useful in the separation from gas mixtures of such complexible ligands as olefins, acetylenes, aromatics, and carbon monoxide. For example, in U.S. Pat. No. 3,651,159, Long et al. disclosed a process in which a sorbent solution of cuprous aluminum tetrahalide in toluene was used to separate ethylene, propylene, and other complexible ligands from a feed stream. The complexed ligands were recovered by ligand exchange with toluene. The resulting solution of cuprous aluminum tetrahalide.toluene in toluene was recycled and used to separate additional quantities of the complexible ligands from the feed stream. Walker et al. in U.S. Pat. No. 3,647,843 disclosed a process in which a hydrocarbon pyrolysis gas stream was contacted with a cuprous aluminum tetrachloride solution in toluene to separate acetylene from the gas stream as a solution of the complex HC≡CH.CuAlCl$_4$ in toluene. Acetylene was stripped from this complex, and the cuprous aluminum tetrachloride.toluene complex was recycled.

In processes such as those disclosed by Long et al. and Walker et al. in which a liquid sorbent containing a bimetallic salt complex is recycled without purification and is used for long periods of time, there is a gradual increase in the amounts of reaction by-products and other impurities in the liquid sorbent unit sufficient impurity is present to interfere with the efficient operation of the process. For example, any water that in present in the gas stream reacts with the liquid sorbent $M_I M_{II} X_n$·Aromatic to form the complex $M_I M_{II} X_n \cdot M_{II} OX$·Arommatic, any ammonia that is present reacts to form the complex $M_I M_{II} X_n \cdot NH_3 M_{II} X_{n-1}$, and any methanol that is present reacts to form the complex $M_I M_{II} X_n \cdot CH_3 O M_{II} X_{n-1}$. These complexes and other contaminants that have limited solubility in the liquid sorbent tend to precipitate from the sorbent in the cooler parts of the apparatus, thereby forming a sludge that coats heat exchangers, clogs lines, and otherwise fouls the equipment. When this occurs, it is necessary to purify or discard the liquid sorbent and to remove the sludge from the equipment. These procedures are time-consuming and costly.

In accordance with this invention, it has been found that the complexes formed by the reaction of water and other reactive impurities in a gas stream with the bimetallic salt complex $M_I M_{II} X_n$·Aromatic are reactive and that they can be used to remove additional amounts of these impurities from the gas stream.

When a gas stream that contains at least one complexible ligand is contacted with a purification medium that comprises the bimetallic salt complex $M_I M_{II} X_n$·Aromatic and one or more of the aforementioned reactive complexes, substantially all of the reactive impurities are removed from it. The purified gas stream can then be contacted with the liquid sorbent that separates the complexible ligands from it. When the purified gas stream is used in this process, the liquid sorbent can be recycled for long periods of time without requiring purification to remove contaminants that can form solid deposits in the apparatus.

In the process of this invention, a gas stream that contains complexible ligands and that is to be contacted with a liquid sorbent that comprises a bimetallic salt complex having the generic formula $M_I M_{II} X_n$·Aromatic to separate the complexible ligands from it is first treated with a purification medium that comprises (a) at least one complex formed from the bimetallic salt complex $M_I M_{II} X_n$·Aromatic and water or another reactive impurity in the gas stream, (b) the bimetallic salt complex $M_I M_{II} X_n$·Aromatic, and (c) a monocyclic aromatic hydrocarbon having 6 to 12 carbon atoms. Gas streams that have been treated in this way contain less than 5 ppm of the reactive impurities; in most cases they contain less than 1 ppm of these impurities. The purified gas stream can be used in processes such as those described in U.S. Pat. No. 3,647,843 and U.S. Pat. No. 3,651,159 without causing the formation of deposits of reaction by-products in the apparatus. Because the solid products formed by the reaction of the impurities with the liquid sorbent are collected in a single vessel rather than distributed throughout the apparatus, they can be removed from the system and treated to recover valuable metals from them without interfering with the separation of ligands from the gas stream. This purification procedure has the further advantage of allowing the liquid sorbent to be recycled for long periods of time without purification. In addition, it is economical in that it uses a material that previously was a waste product that interfered with the efficient operation of the process to purify the gas stream before it is used in the process.

The gas streams that are purified by means of the purification process of this invention contain complexible ligands, such as olefins having 2 to 20 carbon atoms, acetylenes having 2 to 6 carbon atoms, aromatics having 6 to 12 carbon atoms, carbon monoxide, and mixtures thereof, that are known to react with the bimetallic salt complexes $M_I M_{II} X_n$·Aromatic. Illustrative of these gas streams are acetylene process off-gases and gas streams resulting from the cracking of light petroleum fractions and waxes.

The liquid sorbents that are used in the process of this invention are solutions of a bimetallic salt complex in an aromatic hydrocarbon or a halogenated aromatic hydrocarbon. The bimetallic salt complexes have the generic formula $M_I M_{II} X_n$·Aromatic. $M_I$ is a Group I-B metal; that is, copper, silver, or gold. Copper (I) is the preferred metal. $M_{II}$ is a Group III-A metal; that is boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by n. Aromatic is a monocyclic aromatic hydrocarbon or halogenated hydrocarbon having 6 to 12 carbon atoms, and preferably 6 to 9 carbon atoms, such as benzene, toluene, ethylbenzene, xylene, mesitylene, chlorobenzene, chlorotoluene, or chloroxylene. It is preferably toluene. Illustrative of these bimetallic salt complexes are the following: CuBF$_4$.benzene, CuBCl$_4$.benzene, AgBF$_4$.mesitylene, AgBCl$_4$.xylene, AgAlCl$_4$.xylene, AgAlBr$_4$.benzene, CuGaCl$_4$.toluene, CuInI$_4$.chlorobenzene, CuTlI$_4$.p-chlorotoluene, and the like. The preferred bimetallic salt complexes are CuAlCl$_4$.toluene and CuAlBr$_4$.toluene. The aromatic hydrocarbon in which the bimetallic salt complex is dissolved is usually and preferably the same as that used in the preparation of the bimetallic salt complex, but if desired it may be a different one. The total amount of aromatic hydrocarbon in the liquid sorbent, that is, the amount in the bimetallic salt complex plus the amount used as solvent, is at least 10 mole percent of the amount of the bimetallic salt $M_IM_{II}X_n$ that is present. It is preferred that the amount of aromatic hydrocarbon be 100 to 250 mole percent of the amount of the bimetallic salt. The particularly preferred liquid sorbents contain 25 to 75 percent by weight of CuAlCl$_4$.toluene in toluene.

The reactive impurities that can be removed from the gas streams by the process of this invention are compounds that are stronger Lewis bases than the halides of Group I-B metals and that react irreversibly with the bimetallic salt complex $M_IM_{II}X_n$.Aromatic. Among these compounds are water; ammonia and amines, such as triethylene diamine and triphenylamine; alcohols, such as methanol, ethanol, propanol, butanol, and triphenylmethyl carbinol; hydrogen cyanide; and such sulfur-containing compounds as hydrogen sulfide, methyl mercaptan, ethyl mercaptan, propyl mercaptan, methyl sulfide, ethyl sulfide, ethyl disulfide, propyl disulfide, and the like. The gas stream may contain one or more of these impurities.

While the novel purification procedure can be used to remove larger amounts of the aforementioned reactive impurities, it is preferably applied to gas streams that contain not more than 5 mole percent of such compounds. In most cases, the gas streams that are purified in this way contain not more than 1 mole percent of these compounds. When the gas stream contains more than about 3 mole percent of water and/or another reactive impurity, it is often advantageous to treat it first with a conventional drying agent, such as a molecular sieve, or to distill it to reduce its content of the impurity to less than 1 mole percent before it is brought into contact with the purification medium.

The gas streams that have been purified by the process of this invention contain less than 5 ppm and usually less than 1 ppm of the reactive impurities.

In a preferred embodiment of the invention, water is removed from a gas stream that contains at least one complexible ligand, such as ethylene, propylene, acetylene, or carbon monoxide, by contacting the gas stream with a purification medium that comprises CuAlCl$_4$.Aromatic, CuAlCl$_4$.AlOCl Aromatic, and an aromatic hydrocarbon. During the purification step which is carried out at a temperature between −10°C. and the boiling point of the aromatic hydrocarbon at pressures between 0.5 atmosphere and 30 atmospheres and preferably at ambient temperature at 1 atmosphere to 10 atmospheres, the water in the gas stream reacts with the bimetallic salt complex CuAlCl$_4$.Aromatic to form the complex CuAlCl$_4$.AlOCl. Aromatic and/or with the latter complex to form AlOCl and cuprous chloride. The reactions that take place are shown in the following equations in which the aromatic hydrocarbon is toluene:

(1) 2CuAlCl$_4$.toluene + H$_2$O → HCl↑ + CuCl↓ + CuAlCl$_4$.Al(OH)Cl$_2$.toluene (2) CuAlCl$_4$.Al(OH)Cl$_2$.toluene → HCl↑ + CuAlCl$_4$.AlOCl.toluene↓

(3) 2CuAlCl$_4$.AlOCl.toluene + H$_2$O → 2AlOCl + 2CuCl + 2HCl + 2toluene

At the start of the process, the purification medium may be a solution of CuAlCl$_4$.toluene in toluene. As soon as this medium is contacted with a gas stream that contains water, the complex CuAlCl$_4$.AlOCl.toluene is formed. The purification medium then contains the complex CuAlCl$_4$.toluene, the complex CuAlCl$_4$.AlOCl.toluene, and toluene. As has been indicated, both of these complexes will react with water in the gas stream.

The rates at which the aforementioned reactions take place and the amount of water that will react with the complexes are dependent to a large extent upon the concentration of CuAlCl$_4$ in the purification medium. It is therefore preferred that the sludge that results from reactions (1) and (2) be allowed to remain in the purification medium and that sufficient CuAlCl$_4$.toluene be added periodically to replace that which has reacted irreversibly with water to form non-reactive compounds.

When the flow characteristics of the gas stream through the purification medium indicate that the medium contains an excessive amount of non-reactive compounds, the spent medium may be replaced by fresh purification medium. The spent medium may then be reactivated by allowing the cuprous chloride and aluminum oxychloride to settle and then separating them, for example, by filtration or decantation. The CuAlCl$_4$ concentration of the purification medium is then brought to the desired level by the addition of CuAlCl$_4$.toluene. If desired, the complex CuAlCl$_4$.AlOCl.toluene may be added to the medium instead of or in addition to the bimetallic salt complex CuAlCl$_4$.toluene.

Because of its high metal content, the solid material that is recovered during the reactivation of the purification medium cannot be discarded without creating pollution problems. In addition, it is economically desirable to recover from it the copper, which is the most costly component of the purification medium. Any suitable and convenient process may be used for the separation of copper from the recovered solid material. For example, the solids can be dissolved in an aqueous ammonium chloride solution and this solution treated with aluminum to reduce the Cu(NH$_3$)$_2^+$ to copper. After separation of the copper from it, the solution of aluminum salts is generally discarded.

In other preferred embodiments of the invention, the purification medium is used to remove small amounts of ammonia, methanol, hydrogen sulfide, and/or hydrogen cyanide from gas streams. In each case the impurity is removed by contacting the gas stream with a purification medium that comprises the bimetallic salt complex CuAlCl$_4$.Aromatic and the complex formed by the reaction of the impurity with CuAlCl$_4$.Aromatic in an aromatic hydrocarbon.

The invention is further illustrated by the following examples.

EXAMPLE 1

A. A liquid sorbent that contained 28.6 mole percent of cuprous aluminum tetrachloride and 71.4 mole percent of toluene was prepared by adding 1.1 moles of cuprous chloride to 1 mole of anhydrous aluminum chloride in toluene. The resulting solution was filtered to remove unreacted cuprous chloride and insoluble impurities from it.

B. A gas stream obtained by the pyrolysis of natural gas had the following composition:

| | |
|---|---|
| Hydrogen | 55.0 Mole Percent |
| Carbon monoxide | 28.0 |
| Acetylene | 7.5 |
| Methane | 6.0 |
| Carbon dioxide | 2.5 |
| Water | 1.0 |

This gas was fed at room temperature and 19 psia pressure to a pretreatment column in which it was contacted with a purification medium that comprised the liquid sorbent of Example 1A. The gas stream that left the column contained less than 1 ppm of water.

C. The gas stream from which the water had been removed was fed into an absorption column in which it was contacted with an amount of the liquid sorbent of Example 1A that contained at least sufficient cuprous aluminum tetrachloride to react with all of the acetylene and carbon monoxide in the feed gas. The acetylene and carbon monoxide reacted with the liquid sorbent in the absorption column to form a solution that contained the acetylenecuprous aluminum tetrachloride complex and the carbon monoxidecuprous aluminum tetrachloride complex. This solution was fed to a stripping column in which it was brought into contact with benzene vapor at 80°C. The mixture of benzene vapor and carbon monoxide that left the column was cooled to 25°C. to separate the carbon monoxide from the benzene. The sorbent solution which then contained cuprous aluminum tetrachloride and the acetylene-cuprous aluminum tetrachloride complex was fed to a stripping column in which it was brought into contact with benzene vapor at 95°C. The vapor that left the column was cooled to condense the benzene and separate it from the acetylene. The stripped sorbent was returned to the absorption column where it reacted with additional amounts of carbon monoxide and acetylene in the gas stream.

D. The passage of the pyrolysis gas through the pretreatment column and the absorption column was continued until a total of about 100 moles of water had been removed from the gas. Additional amounts of the liquid sorbent of Example 1A were added periodically to replace that which had reacted with the water to form CuCl and AlOCl.

When the passage of the gas through the pretreatment column had been discontinued, the purification medium was shown by analysis to be a suspension of $CuAlCl_4.AlOCl.toluene$, CuCl, and AlOCl in a solution of $CuAlCl_4.toluene$ in toluene. At the same time the liquid sorbent in the absorption column was found to contain only a very small amount of solid material.

E. The purification medium was heated to dissolve the $CuAlCl_4.AlOCl.toluene$ and then filtered. The separated CuCl and AlOCl were dissolved in 10% aqueous ammonia, and the resulting solution was treated with aluminum to reduce the $Cu(NH_3O)_2^+$ to copper metal. The copper was recovered, and the remaining solution which contained soluble aluminum and ammonium salts was discarded.

EXAMPLE 2

A. A liquid sorbent that contained 25 percent by weight of $CuAlCl_4.toluene$ in toluence was placed in a purification system that consisted of two 2½ inches diameter gas columns, the first of which was 25 inches long and the second of which was 6 inches long. The columns were packed with glass beads.

B. A pyrolysis gas stream that contained 460 ppm of water as determined by dewpoint analysis was passed through the purification system of Example 2A at the rate of 0.0256 cu. ft./min. for 2.6 hours. The gas leaving the second column of the purification system contained less than 1 ppm of water.

C. The purified gas stream was passed through the absorption column described in Example 1C to remove acetylene and carbon monoxide from it.

D. When the passage of the gas stream through the purification system and the absorption column had been completed, the purification medium in the columns of the purification system was found to be a suspension of $CuAlCl_4.AlOCl.toluene$, CuCl, and AlOCl in a solution of $CuAlCl_4.toluene$ in toluene. The liquid sorbent in the absorption column was found to be a solution of $CuAlCl_4.toluene$ in toluene and to contain substantially no suspended solid material.

EXAMPLE 3

A. An acetylene process off-gas that contained about 30 mole percent of carbon monoxide, 64 mole percent of hydrogen, 5 mole percent of methane, 0.8 mole percent of other organic compounds, and 0.2 mole percent of ammonia was fed into the purification system described in Example 2A at the rate of 0.0256 cu. ft./min. for 15 minutes. The gas leaving the first column contained 25 ppm. of ammonia; that leaving the second column contained less than 1 ppm of ammonia.

B. The gas stream leaving the purification system was passed through the absorption column described inn Example 1C to remove carbon monoxide from it.

C. When the passage of the gas through the purification system and the absorption column had been completed, the purification medium in the columns of the purification system was found to contain $CuAlCl_4.NH_3AlCl_3.toluene$ and $CuAlCl_4.toluene$. The liquid sorbent in the absorption column was found to be a solution of $CuAlCl_4.toluene$.

In a similar way, each of the other reactive impurities mentioned hereinbefore can be removed from a gas stream containing at least one complexible ligand before said gas stream is contacted with a liquid sorbent containing the bimetallic salt complex $M_IM_{II}X_n$.Aromatic to separate the complexible ligand from it.

What is claimed is:

1. In the process for the separation of a complexible ligand selected from the group consisting of olefins having 2 to 20 carbon atoms, acetylenes having 2 to 6 carbon atoms, aromatics have 6 to 12 carbon atoms, carbon monoxide and mixtures thereof from a gas stream that contains said complexible ligand and reactive impurities selected from the group consisting of water, alcohols, ammonia, amines, hydrogen cyanide, hydrogen sulfide, alkyl mercaptans, alkyl sulfides, and mixtures thereof; wherein the gas stream is contacted with a liquid sorbent that is a solution in an aromatic hydrocarbon of a bimetallic salt complex having the formula $CuAlCl_4.Aromatic$, wherein Aromatic is a monocyclic aromatic hydrocarbon having 6 to 12 carbon atoms, thereby forming a reaction mixture comprising a solution of a complex of the bimetallic salt complex and the ligand in the liquid sorbent, the reaction mixture is separated from the gas stream, the ligand is separated from the reaction mixture, and the reaction mixture is recycled, the improvement that comprises removing said reactive impurities from the gas stream before the gas stream is contacted with said liquid sorbent by a. contacting the gas stream that contains said complexible ligand and up to 3 mole percent of said impurities with siad liquid sorbent, thereby forming a purification medium that comprises the bimetallic salt complex $CuAlCl_4$.Aromatic, at least one product of the reaction of the reactive impurities with the bimetallic salt complex $CuAlCl_4$.Aromatic, and the aromatic hydrocarbon;

b. separating a purified gas stream that contains the complexible ligand and less than 1 ppm of the reactive impurities from said purification medium;

c. contacting said purification medium with the gas stream that contains the complexible ligand and up to 3 mole percent of reactive impurities;

d. seperating a purified gas stream that contains the complexible ligand and less than 1 ppm of reactive impurities from the purification medium;

e. repeating steps c) and d) until the purification medium contains an amount of solid reaction products that interferes with the passage of the gas stream through said medium; and f. recovering the complexible ligand from the purified gas stream that is separated from the purification medium in steps b) and d).

2. The process of claim 1 wherein a. a gas stream that contains a complexible ligand selected from the group consisting of olefins having 2 to 20 carbon atoms, acetylenes having 2 to 6 carbon atoms, aromatics having 6 to 12 carbon atoms, carbon monoxide, and mixtures thereof and not more than 1 mole percent of water is contacted with a liquid sorbent that is a solution in an aromatic hydrocarbon of $CuAlCl_4$.Aromatic, wherein Aromatic is a monocyclic aromatic hydrocarbon having 6 to 12 carbon atoms, thereby forming a purification medium that comprises $CuAlCl_4$.AlOCl.Aromatic, $CuAlCl_4$.Aromatic, CuCl, and the aromatic hydrocarbon;

b. a purified gas stream that contains the complexible ligand and less than 1 ppm of water is separated from the purification medium;

c. the purification medium is contacted with the gas stream that contains the complexible ligand and up to 1 mole percent of water;

d. a purified gas stream that contains the complexible ligand and less than 1 ppm of water is separated from the purification medium;

e. steps c) and d) are repeated until the purification medium contains an amount of suspended $CuAlCl_4$.AlOCl.Aromatic, AlOCl, and CuCl that interferes with the passage of the gas stream through the medium, and f. the complexible ligand is recovered from the purified gas stream that is separated from the purification medium in steps b) and d).

3. The process of claim 2 wherein the liquid sorbent is a solution of $CuAlCl_4$.toluene in toluene and the purification medium comprises a suspension of $CuAlCl_4$.AlOCl.toluene, AlOCl, and CuCl in a solution of $CuAlCl_4$.toluene in toluene.

4. The process of claim 1 wherein the gas stream contains as reactive impurity less than 1 mole percent of ammonia, and the purification medium comprises $CuAlCl_4.NH_3AlCl_3$.Aromatic, CuCl, $CuAlCl_4$.Aromatic, and an aromatic hydrocarbon.

5. The process of claim 1 wherein the gas stream contains as reactive impurity less than 1 mole percent of methanol, and the purification medium comprises $CuAlCl_4.CH_3OHAlCl_3$.Aromatic, CuCl, $CuAlCl_4$.Aromatic, and an aromatic hydrocarbon.

* * * * *

UNITED STATES PATENT OFFICE
CERTIFICATE OF CORRECTION

PATENT NO. : 3,960,910
DATED : June 1, 1976
INVENTOR(S) : Jerome R. Sudduth and Donald A. Keyworth It is certified that error appears in the above-identified patent and that said Letters Patent are hereby corrected as shown below:

Column 1, line 41, change "unit" to -- until --.

Column 1, line 46, change "Arommatic" to -- Aromatic --.

Column 5, line 28, change "acetylenecuprous" to -- acetylene cuprous --.

Column 5, line 29, change "monoxidecuprous" to -- monoxide cuprous --.

Column 5, line 65, change "Cu(NH3O)$_2^+$" to -- Cu(NH3)$_2^+$ --.

Column 6, line 5, change "inches" to -- inch --.

Column 6, line 39, change "inn" to -- in --.

Column 6, line 47, after "toluene" insert -- in toluene --.

Column 7, line 12, change "siad" to -- said --.

Column 7, line 24, change "seperating" to -- separating --.

Signed and Sealed this

Tenth Day of August 1976

[SEAL]

Attest:

RUTH C. MASON
Attesting Officer

C. MARSHALL DANN
Commissioner of Patents and Trademarks